HI US011793433B2

(12) United States Patent
Zhang et al.

(10) Patent No.: US 11,793,433 B2
(45) Date of Patent: Oct. 24, 2023

(54) BLOOD COLLECTION DEVICE (71) Applicant: TIANJIN HUAHONG TECHNOLOGY CO., LTD., Tianjin (CN)

(72) Inventors: Libo Zhang, Tianjin (CN); Chengzhe Cui, Tianjin (CN)

(73) Assignee: TIANJIN HUAHONG TECHNOLOGY CO., LTD., Tianjin (CN)

( * ) Notice: Subject to any disclaimer, the term of this patent is extended or adjusted under 35 U.S.C. 154(b) by 435 days.

(21) Appl. No.: 17/204,116

(22) Filed: Mar. 17, 2021

(65) Prior Publication Data
US 2021/0290124 A1 Sep. 23, 2021

(30) Foreign Application Priority Data
Mar. 18, 2020 (CN) .......................... 202010189142.2

(51) Int. Cl.
*A61B 5/151* (2006.01)
*A61B 5/15* (2006.01)

(52) U.S. Cl.
CPC .... *A61B 5/15113* (2013.01); *A61B 5/150022* (2013.01); *A61B 5/15029* (2013.01);
(Continued)

(58) Field of Classification Search
CPC ........ A61B 5/150022; A61B 5/150259; A61B 5/15029; A61B 5/150442;
(Continued)

(56) References Cited

U.S. PATENT DOCUMENTS 4,856,515 A * 8/1989 Turner ............... A61B 5/15113
606/182
2010/0010528 A1* 1/2010 Shi ..................... A61B 5/15113
606/182
(Continued)

FOREIGN PATENT DOCUMENTS

CN  110151194 A  8/2019

OTHER PUBLICATIONS

Extended European Search Report for corresponding European Application No. 21163524.8, dated Sep. 23, 2021. 8 pages.

*Primary Examiner* — Jocelin C Tanner
(74) *Attorney, Agent, or Firm* — Leason Ellis LLP (57) ABSTRACT

The present disclosure relates to a blood collection device, including: a shell; a blade seat, arranged in the shell; an elastic component for providing an elastic force for pivoting the blade seat; a triggering portion, including an operating end and an abutting end, wherein the triggering portion has a first position and a second position for pivoting, the operating end extends to the outside of the shell, the abutting end is located in the shell, based on the operation of the operating end, the triggering portion is suitable for pivoting from the first position that prevents the blade seat from pivoting to the second position that allows the blade seat to pivot based on the elastic force of the elastic component, wherein: a cooperation column is arranged in the shell and is located at the upper side of the triggering portion spaced from the triggering portion; and an elastic arm is connected to the upper side of the triggering portion, the end part of the elastic arm includes a blocking portion, the end part of the elastic arm is suitable for being located on one side of the cooperation column when the triggering portion is at the first position, and is located on the other side of the cooperation column when the triggering portion pivots from the first position to the second position, and the blocking portion (Continued)

provides resistance for the end part of the elastic arm while moving from one side of the cooperation column to the other side.

20 Claims, 6 Drawing Sheets

(52) U.S. Cl.
CPC .... *A61B 5/15117* (2013.01); *A61B 5/150442* (2013.01); *A61B 2503/045* (2013.01)

(58) Field of Classification Search
CPC .......... A61B 5/150916; A61B 5/15101; A61B 5/15107; A61B 5/15113; A61B 5/15117; A61B 5/15128; A61B 5/15144; A61B 2502/045
See application file for complete search history.

(56) References Cited

U.S. PATENT DOCUMENTS

2015/0209068 A1    7/2015  Booker et al.
2017/0042459 A1*  2/2017  Shi ..................... A61B 5/15144

\* cited by examiner

BLOOD COLLECTION DEVICE

CROSS-REFERENCE TO RELATED PATENT APPLICATIONS

This application claims the benefit of priority of Chinese Patent Application No. 202010189142.2 filed on Mar. 18, 2020, which is incorporated by reference in its entirety.

TECHNICAL FIELD

The embodiments of the present disclosure relate to the field of medical equipment, in particular to a blood collection device.

BACKGROUND ART

Neonatal heel blood screening refers to the examination of heel blood collected 72 hours after birth. It is mainly aimed at diseases with high incidence rates, without obvious symptoms in the early stage but positive laboratory indicators, which can be diagnosed and treated. At present, there are two kinds of blood collection devices for neonatal heel blood collection: one type is a common peripheral lancing device, collecting blood through acupuncture, which is mainly used in finger pulp blood collection; and the other type is a heel blood collection device specially designed for heel blood collection, collecting blood by means of blade cutting. Compared with existing common peripheral lancing devices, the heel blood collection device has the advantages of large amount of bleeding and light pain, thereby having a good application prospect in the field of neonatal heel blood collection.

However, as being disposable and consumable, the heel blood collection device has many components and thus has a complex structure.

SUMMARY OF THE INVENTION

In order to alleviate or solve the above-mentioned problems, the present disclosure proposes a blood collection device, especially a foot blood collection device, which has the advantages of a small number of components and a simple structure.

According to one aspect of the embodiments of the present disclosure, a blood collection device is provided, including:
a shell, wherein an accommodating cavity is formed in the shell, and the shell has a first opening and a second opening;
a blade seat, pivotally arranged in the accommodating cavity, wherein a blade is arranged to the blade seat, and the blade is suitable for being exposed from the shell through the first opening when the blade seat pivots;
an elastic component, arranged in the accommodating cavity, wherein one end of which is connected to the shell, and the other end of which is connected to the blade seat to provide an elastic force for pivoting the blade seat;
a triggering portion, wherein the triggering portion includes an operating end and an abutting end that are respectively arranged at two ends thereof, the triggering portion is suitable for pivoting around a pivot shaft arranged in the shell, the operating end extends from the second opening to the outside of the shell, the abutting end is located in the accommodating cavity, based on the operation of the operating end, the triggering portion is suitable for pivoting from a first position to a second position, at the first position, the abutting end is suitable for abutting against the blade seat (30) to prevent the blade seat from pivoting, and at the second position, the abutting end deviates from the blade seat to allow the blade seat to pivot based on the elastic force of the elastic component,
wherein:
a first cooperation column is arranged in the shell and is located at the upper side of the triggering portion spaced from the triggering portion; and
an elastic arm is connected to the upper side of the triggering portion, the end part of the elastic arm is located in the accommodating cavity and includes a blocking portion, the end part of the elastic arm is suitable for being located at one side of the first cooperation column when the triggering portion is at the first position, and is located at the other side of the first cooperation column when the triggering portion pivots from the first position to the second position, and the blocking portion provides resistance for the end part of the elastic arm while moving from one side of the first cooperation column to the other side.

According to another aspect of the embodiments of the present disclosure, a blood collection device is provided, including:
a shell, wherein an accommodating cavity is formed in the shell, and the shell has a first opening and a second opening;
a blade seat, pivotally arranged in the accommodating cavity, wherein a blade is arranged to the blade seat, and the blade is suitable for being exposed from the shell through the first opening when the blade seat pivots;
an elastic component, arranged in the accommodating cavity, wherein one end of which is connected to the shell, and the other end of which is connected to the blade seat to provide an elastic force for pivoting the blade seat;
a triggering portion, wherein the triggering portion includes an operating end and an abutting end that are respectively arranged at two ends thereof, the triggering portion is suitable for pivoting around a pivot shaft arranged in the shell, the operating end extends from the second opening to the outside of the shell, the abutting end is located in the accommodating cavity, based on the operation of the operating end, the triggering portion is suitable for pivoting from a first position to a second position, at the first position, the abutting end is suitable for abutting against the blade seat to prevent the blade seat from pivoting, and at the second position, the abutting end deviates from the blade seat to allow the blade seat to pivot based on the elastic force of the elastic component,
wherein:
a first cooperation column is arranged in the shell and is located at the upper side of the triggering portion spaced from the triggering portion;
a second cooperation column is arranged in the shell and is located at the lower side of the triggering portion spaced from the triggering portion;
an elastic arm is connected to the upper side of the triggering portion, the end part of the elastic arm is provided with a bending portion, the bending portion is arranged in the accommodating cavity and is suitable for cooperating with the first cooperation column, in the case that the triggering portion is at the first position, an upper side face of the bending portion abuts against an outer circumferential surface on the lower side of the first cooperation column;

the tail end of the bending portion is bent upward to provide resistance for the elastic arm to disengage from the first cooperation column when the triggering portion is at the first position;

and a guide arm is connected to the lower side of the triggering portion, and during the process when the triggering portion rotates from the first position to the second position, the guide arm is suitable for sliding over the second cooperation column at the outer side of the second cooperation column when abutting against the outer circumferential surface of the second cooperation column.

DETAILED DESCRIPTION OF THE EMBODIMENTS

The technical solutions of the present disclosure will be further described below in detail through embodiments and in conjunction with the drawings. In the specification, the same or similar reference signs indicate the same or similar components. The following descriptions of the embodiments of the present disclosure with reference to the drawings are intended to explain the general inventive concept of the present disclosure, and should not be understood as a limitation to the present disclosure.

Figure 1:
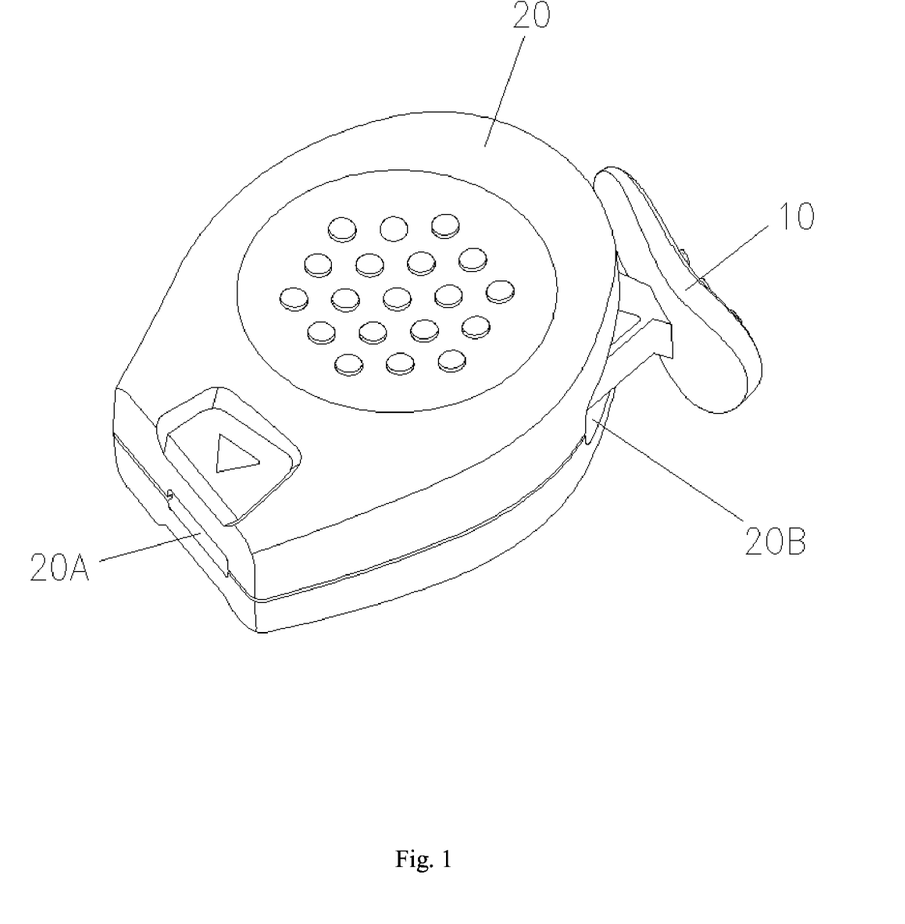
FIG. 1 is a space diagram of a blood collection device according to an exemplary embodiment of the present disclosure.
Figure 2:
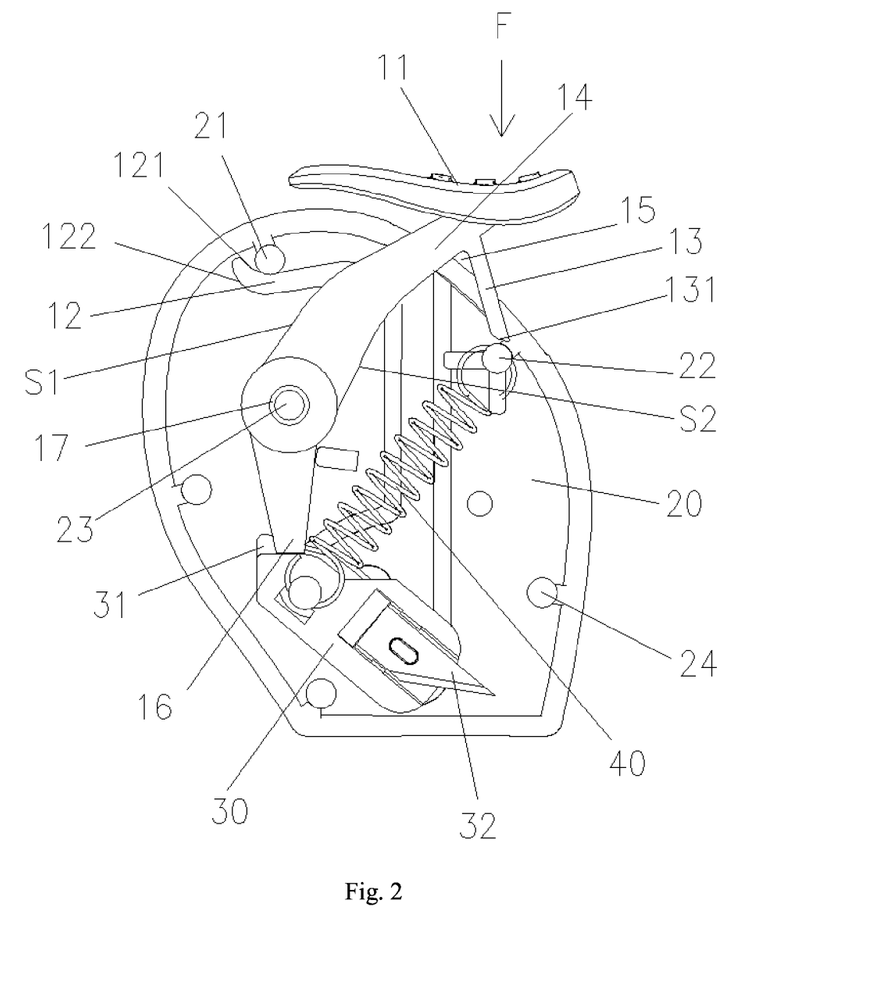
FIG. 2 is a schematic diagram of connection of components in a blood collection device according to an exemplary embodiment of the present disclosure, wherein a state of the blood collection device before use is shown.
Figure 3:
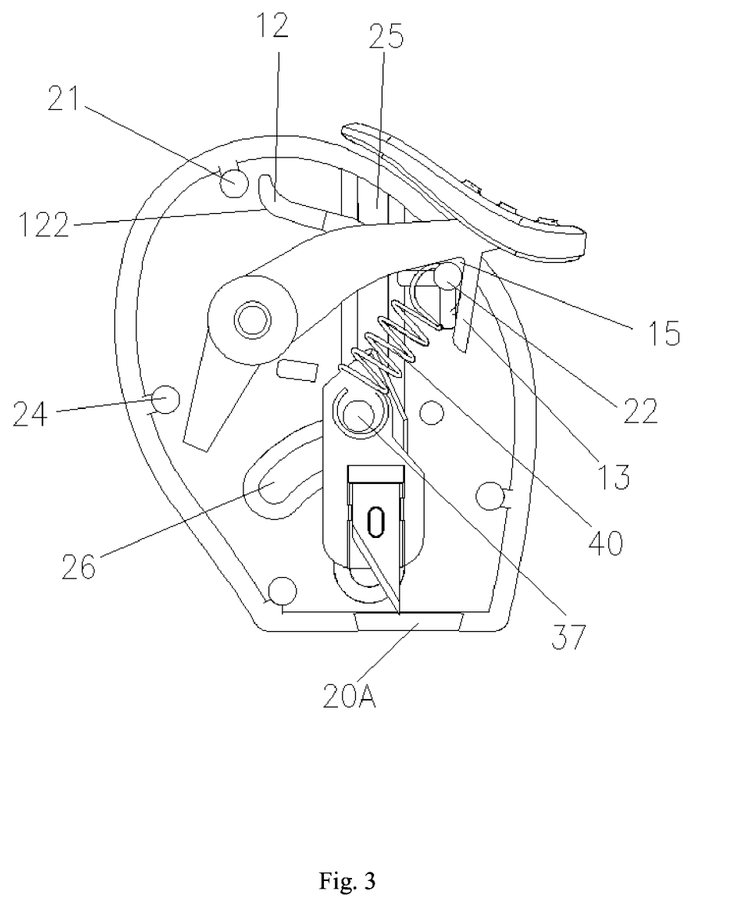
FIG. 3 is a schematic diagram of connection of components in a blood collection device according to an exemplary embodiment of the present disclosure, wherein a state of the blood collection device after use is shown.
Figure 4:
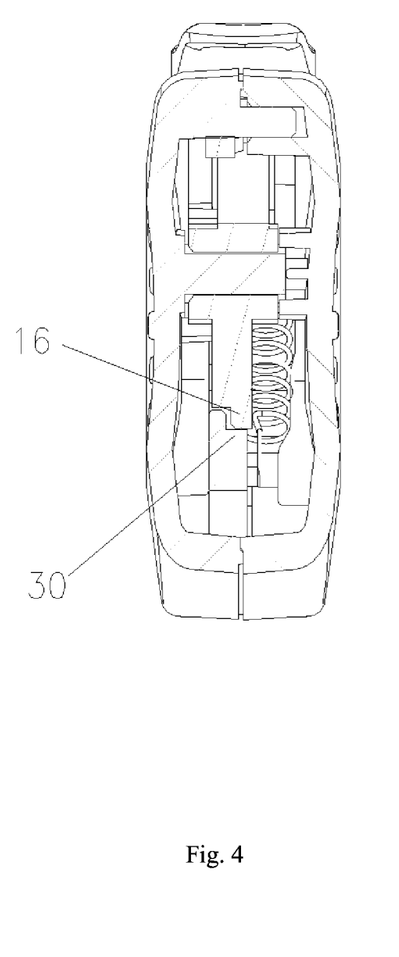
FIG. 4 is a section view of a blood collection device according to an exemplary embodiment of the present disclosure, wherein a cooperation state of an abutting end of a triggering portion and a blade seat before the use of the blood collection device is shown.
Figure 5:
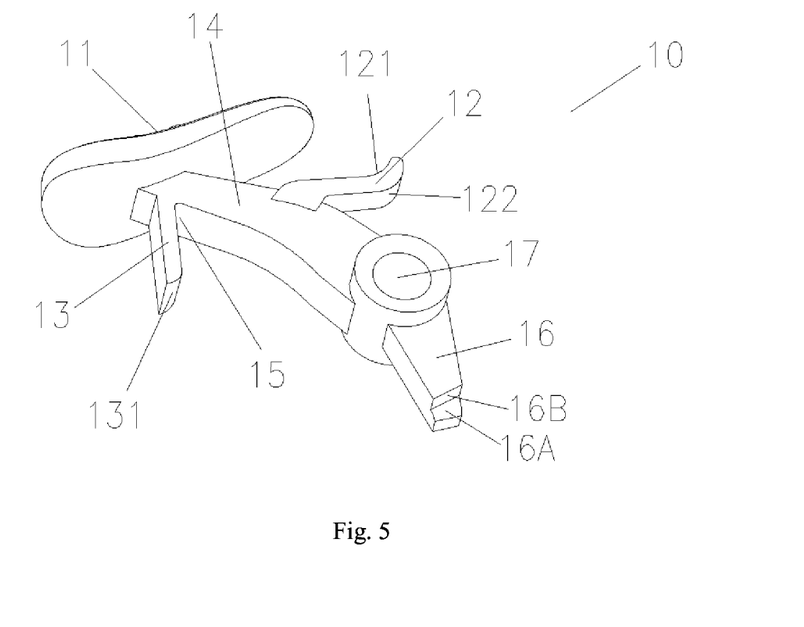
FIG. 5 is a three-dimensional schematic diagram of a triggering portion of a blood collection device according to an exemplary embodiment of the present disclosure.
Figure 6:
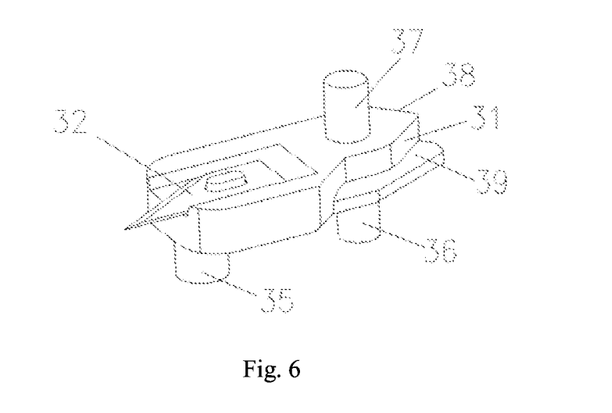
FIG. 6 is a structural schematic diagram of a blade seat of a blood collection device according to an exemplary embodiment of the present disclosure.

The blood collection device according to the present disclosure will be exemplarily described below with reference to FIG. 1 to FIG. 6. As shown in the figures, the blood collection device according to an exemplary embodiment of the present disclosure includes:

a shell 20, wherein an accommodating cavity is formed in the shell, and the shell has a first opening 20A and a second opening 20B, as shown in FIG. 1;

a blade seat 30, as shown in FIG. 2 and FIG. 6, pivotally arranged in the accommodating cavity, wherein a blade 32 is arranged to the blade seat 30, and the blade 32 is suitable for being exposed from the shell 20 through the first opening 20A when the blade seat 30 pivots;

an elastic component 40, as shown in FIG. 2, arranged in the accommodating cavity, wherein one end of which is connected to the shell 20, in FIG. 2, the elastic component is connected to a second cooperation column 22 mentioned below, and the other end of the elastic component 40 is connected to the blade seat 30 to provide an elastic force for pivoting the blade seat;

a triggering portion 10, as shown in FIG. 5, wherein the triggering portion 10 includes an operating end 11 and an abutting end 16 that are respectively arranged at two ends thereof, the triggering portion 10 is suitable for pivoting around a pivot shaft 23 arranged in the shell 20 (in an optional embodiment, the pivot shaft 23 cooperates with a through hole 17 formed in the triggering portion 10, it should be pointed out that although the pivot shaft here is shown as being fixed to the shell 10 in the drawings, the pivot shaft in the claims of the present disclosure also includes a situation where the pivot shaft is fixed to the triggering portion and a pivot hole cooperating with the same is formed in the shell), the operating end 11 extends from the second opening 20B to the outside of the shell 20, the abutting end 16 is located in the accommodating cavity, based on the operation of the operating end 11, the triggering portion 10 is suitable for pivoting from a first position (the position in FIG. 2) to a second position (the position in FIG. 3), at the first position, the abutting end 16 is suitable for abutting against the blade seat 30 to prevent the blade seat from pivoting (referring to FIG. 2 and FIG. 4), and at the second position, the abutting end 16 deviates from the blade seat 30 to allow the blade seat 30 to pivot based on the elastic force of the elastic component 40, wherein:

as shown in FIG. 2, a first cooperation column 21 is arranged in the shell 20 and is located at the upper side of the triggering portion spaced from the triggering portion 10, and it should be noted that, in the present disclosure, being located at the upper side of the triggering portion indicates a position on the side S1 of the triggering portion 10;

as shown in FIG. 2, a second cooperation column 22 is arranged in the shell 20 and is located at the lower side of the triggering portion spaced from the triggering portion 10, and it should be noted that, in the present disclosure, being located at the lower side of the triggering portion indicates a position on the side S2 of the triggering portion 10;

as shown in FIG. 2 and FIG. 5, an elastic arm 12 is connected to the upper side of the triggering portion 10, the end part of the elastic arm 12 is provided with a bending portion, the bending portion is arranged in the accommodating cavity and is suitable for cooperating with the first cooperation column 21, in the case that the triggering portion 10 is at the first position, as shown in FIG. 2, an upper side face 121 of the bending portion abuts against an outer circumferential surface on the lower side of the first cooperation column 21 (in the present disclosure, the lower side of the cooperation column indicates one side close to the first opening 20A in a vertical direction at the position as shown in FIG. 2);

as shown in FIG. 2 to FIG. 3 and FIG. 5, the tail end of the bending portion is bent upward to provide resistance for the elastic arm 12 to disengage from the first cooperation column 21 when the triggering portion 10 is at the first position; and as shown in FIG. 2 and FIG. 5, a guide arm 13 is connected to the lower side of the triggering portion 10, and during the process when the triggering portion 10 rotates from the first position to the second position, the guide arm 13 is suitable for sliding over the second cooperation column at the outer side of the second cooperation column 22 when abutting against the outer circumferential surface of the second cooperation column 22. In the present disclosure, the outer side of the second cooperation column indicates one side of the second cooperation column closer to a side wall of the shell at the position as shown in FIG. 2.

In a further embodiment, the bending portion is bent upward, and can also cause the tail end of the elastic arm to side toward the side wall of the shell when the tail end of the elastic arm abuts against the first cooperation column.

As shown in FIG. 2 and FIG. 5, the end part of the guide arm 13 is provided with a guide surface 131, and during the process when the triggering portion 10 rotates from the first position to the second position, the guide surface 131 is suitable for guiding the guide arm 13 to slide over the second cooperation column at the outer side of the second cooperation column 22.

Furthermore, as shown in FIG. 2, an upper side face 121 of the tail end of the bending portion is suitable for abutting against the outer circumferential surface of the first cooperation column 21 when the triggering portion is at the first position. As can be understood, during the process when the triggering portion 10 rotates from the second position toward the first position, as shown in FIG. 3, a lower side face 122 of the tail end of the bending portion abuts against the first cooperation column 21 to prevent the triggering portion 10 from rotating from the second position toward the first position.

It should be pointed out that, in the present disclosure, the upper side face of the bending portion or the upper side face of the tail end of the bending portion refers to, for example, in the case of the position as shown in FIG. 2, the surface or upper side face 121 of the bending portion that is suitable for being engaged with the outer circumferential surface of the first cooperation column 21; and the lower side face of the bending portion or the lower side face of the tail end of the bending portion refers to, for example, in the case of the position as shown in FIG. 3, the surface or lower side face 122 of the bending portion that is suitable for abutting against the first cooperation column.

In the present disclosure, the bending portion is not limited to the shape or structure shown in FIG. 5, as long as one side face of the bending portion is suitable for engagement with the first cooperation column based on the elasticity of the elastic arm, the bending portion can provide resistance to prevent the end part of the elastic arm from departing from the first cooperation column, and when the triggering portion rotates from the second position to the first position, the other side face of the bending portion is suitable for abutting against the first cooperation column, or, the tail end of the bent part abuts between the first cooperation column and the side wall of the shell to prevent the triggering portion from further pivoting.

As shown in FIG. 5, the included angle part between the guide arm 13 and the rod body of the triggering portion or the main body 14 forms a positioning groove 15. As shown in FIG. 3, the second cooperation column 22 is suitable for entering the positioning groove 15.

The operation of the blood collection device based on the above description will be briefly described below.

In use, at first, a blade outlet edge is aligned with a blood collection site. Then, a force F is applied to the operating end or a pressing portion 11, the guide surface 131 guides the guide arm 13 to slide along the second cooperation column or a positioning column 22 until the positioning groove 15 is in contact with the second cooperation column 22, and the rotation of the triggering portion 10 stops.

In one embodiment of the present disclosure, the guide arm 13 and the second cooperation column 22 always move relative to each other in a tangential manner, so that the pressing force used in the triggering process of the blood collection device is continuous and uniform, and false triggering caused by the accidental contact with the triggering portion 10 is avoided. In other words, the guide arm 13 is a straight guide arm, and when the triggering portion 10 is at the first position, the guide arm 13 is opposite to the second cooperation column 22, as shown in FIG. 2; and the distance between the second cooperation column 22 and the pivot shaft 23 (that is, the distance between the central axis of the cooperation column 22 and the central axis of the pivot shaft 23) is greater than or equal to the distance between an accommodating position of the angle-shaped positioning groove and the pivot shaft 23 (the distance corresponds to the distance between the central axis of the cooperation column 22 and the central axis of the pivot shaft 23 in FIG. 3), and at the accommodating position, the second cooperation column 22 is adapted to abut against the guide arm 13 and the main body 14 of the triggering portion at the same time.

Before the blood collection device is triggered, the upper side face 121 of the bending portion contacts with the first cooperation column 21, when the operating end 11 is pressed, the triggering portion 10 rotates clockwise along the pivot shaft 23 to a certain angle, and during this process, the upper side face 121 of the bending portion passes over the first cooperation column 21 based on the elastic deformation of the elastic arm or the elastic deformation of the bending portion itself. In a more specific embodiment, the arc length of the surface of the upper side face 121 of the bending portion that is engaged with the first cooperation column is approximately equal to ¼ length of the circumference of the first cooperation column 21, so that it is easier to pass over the first cooperation column 21 based on the elastic deformation, however, it will also cause some interference, and play a role of preventing accidental triggering together with the sliding friction of the guide arm 13. During this process (that is, in the process of moving from the first position of the triggering portion in FIG. 2 to the second position of the triggering portion in FIG. 3), a pressing plate or the abutting end 16 of the triggering portion moves away from the original position and releases a pressure bearing portion or an abutting surface 31, so that the blade seat 30 of the blood collection device is triggered.

After the positioning groove 15 is in contact with the second cooperation column 22 (the second cooperation column 22 is in contact with the main body 14 of the triggering portion and the guide arm 13 at the same time), the triggering portion 10 stops rotating. In one embodiment of the present disclosure, the distance between the lower side face 122 or the side wall surface of the bending portion and the side wall of the first cooperation column 21 may be, for example, around ¼ length of the circumference of the first cooperation column 21. When someone intends to operate the triggering portion 10 in a reverse direction (i.e., reverse rotation) to restore the triggering portion 10 of the used blood collection device to the original position, the lower side face 122 of the bending portion abuts against the first cooperation column 21, for example, forming external tangent, in this way, when the bending portion is subjected to a reverse action, the tail end of the bending portion will warp upward along its arc to prevent the triggering portion from resetting, the upward warping causes either the tail end of the bending portion to abut against the first cooperation column 21, either abuts between the first cooperation column 21 and the side wall of the shell.

As shown in FIG. 1 and FIG. 4, the shell includes a first shell portion (corresponding to a lower shell in FIG. 1) and a second shell portion (corresponding to an upper shell in FIG. 1), and as shown in FIG. 2 and FIG. 3, the pivot shaft 23, the first cooperation column 21 and the second cooperation column 22 are all arranged to the first shell portion.

The first shell portion may be provided with a plurality of mounting columns 24, the second shell portion is provided with mounting holes (not shown) that cooperate with the plurality of mounting columns 24, and the first shell portion and the second shell portion are engaged with each other based on the cooperation between the mounting columns and the mounting holes.

In a specific embodiment, the mounting columns 24 include the first cooperation column 21 and the second cooperation column 22.

The movement of the blade seat 30 will be exemplarily described below with reference to the drawings.

Figure 7:
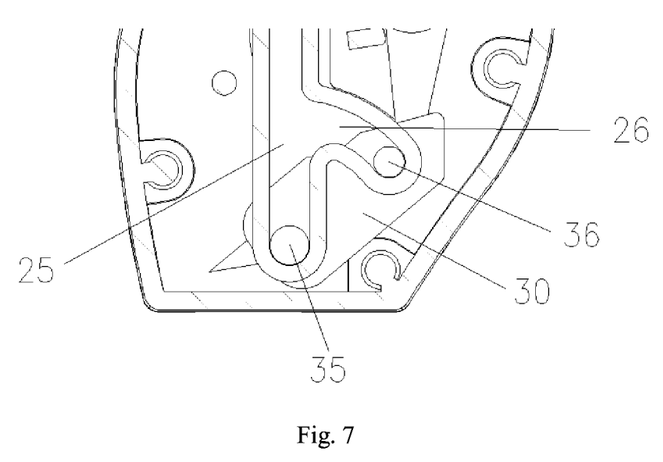
FIG. 7 is an exemplary local section view of a blood collection device according to an exemplary embodiment of the present disclosure, which mainly shows the cooperation between two protrusions of the blade seat and two guide grooves.

As shown in FIG. 6, a first protrusion 35 and a second protrusion 36 are arranged to the blade seat 30; and as shown in FIG. 3 and FIG. 7, the shell is provided with a first guide groove 25 and a second guide portion 26, the first guide groove 25 cooperates with the first protrusion 35, and the extension direction is substantially the same as the blade outlet direction, and the second guide portion 36 cooperates with the second protrusion 26 to guide the second protrusion to enter the first guide groove 25 when the elastic component 40 drives the blade seat 30 to pivot. In the state shown in FIG. 2, the second protrusion 36 is located in the second guide portion 26, and in the state shown in FIG. 3, the second protrusion 36 is already in the first guide groove 25.

As shown in FIG. 6, the blade seat 30 is provided with a fixing column 37, and the elastic component 40 can be fixed on the fixing column 37 to pull the blade seat 30.

More specifically, the first guide groove 25 has a first end (the lower end in FIG. 3) close to the first opening 20A and a second end (the upper end in FIG. 3) far away from the first opening; as shown in FIG. 7, the second guide portion 26 is connected between the first end and the second end of the first guide groove 25; and the elastic component 40 is suitable for driving the blade seat 30 to further move toward the second end of the first guide groove.

As shown in FIG. 7, the second guide portion 26 can have an arc-shaped abutting surface centered on the first protrusion 35.

As shown in FIG. 7, the second guide portion 26 is a second guide groove, and the second guide groove has a first end far away from the first guide groove and a second end communicating with the first guide groove. When the abutting end 16 abuts against the blade seat 30, the first protrusion 35 pivotally abuts against the first end of the first guide groove 25, and the second protrusion 36 pivotally abuts against the first end of the second guide groove.

In an optional embodiment, the upper shell may be provided with a guide groove that cooperates with the first guide groove on the lower shell. If the guiding ability of the guiding groove on the lower shell is sufficient, the upper casing may be not provided with the guide groove.

The abutting cooperation structure of the abutting end 16 and the blade seat 30 will be exemplarily described below with reference to the drawings.

As shown in FIG. 6, the end of the blade seat 30 close to the second protrusion 36 has an abutting surface 31 and an avoidance surface 38 at both sides thereof, and the abutting end 16 of the triggering portion 30 is suitable for abutting against the abutting surface 31. In this way, the pivoting of the blade seat can be prevented.

In a further embodiment, the end of the blade seat 30 close to the second protrusion 36 has a step portion, a vertical surface of the step portion parallel to the thickness direction of the blade seat forms the abutting surface 31, and a horizontal plane of the first step portion vertical to the thickness direction of the blade seat forms a step surface 39. At the same time, as shown in FIG. 5, the abutting end 16 has a blocking cooperation surface 16A that is suitable for extending to cover the step surface 39 and is vertical to the thickness direction of the blade seat 30, and the abutting end 16 has an abutting surface 16B, and the abutting surface 16B is suitable for abutting against the abutting surface 31 to prevent the blade seat from pivoting. As shown in FIG. 5, the abutting end 16 also has a step portion, a vertical surface of the step portion parallel to the thickness direction of the abutting end forms the abutting surface 16B, and a plane of the step portion vertical to the thickness direction of the abutting end 16 forms the blocking cooperation surface 16A.

The use of the blood collection device and the movement of the blade seat 30 according to the present disclosure will be exemplarily described below with reference to the drawings.

At first, a blade outlet is aligned with the blood collection site. Then, an operating portion 11 of the triggering portion 30 is pressed, so that the guide arm 13 slides tangentially along the outer side of the second cooperation column 22. In this process, the bending portion of the elastic arm 12 gradually departs from the first cooperation column 21 based on the elastic deformation of the elastic arm 12.

After the bending portion of the elastic arm 12 deviates from the first cooperation column 21, the abutting end 16 is out of contact with the blade seat 30. At this time, the blade seat 30 is released. Based on the tension of the elastic component, the second protrusion 36 moves along the second guide portion 26, the first protrusion 35 is located at the bottom of the first guide groove 25, and it can be considered that the blade seat 30 basically rotates clockwise around the first protrusion 35 at first. Under the pulling of the elastic component 40, the blade seat 30 first takes the first protrusion 35 as the circle center, and the second protrusion 36 rotates a certain angle along the arc-shaped groove or the second guide portion 26 until it falls into the first guide groove 25. As the second protrusion 36 enters the first guide groove 25, the blade reaches a vertical position (the penetration depth is the largest), furthermore, because the second protrusion 36 cannot move further rightward in the first guide groove 25, so the blade seat 30 can then only move vertically (retract vertically) along the first guide groove 25 under the action of the elastic component. During the clockwise rotation of the blade seat 30, the blade extends out from the blade outlet to collect blood. Immediately afterwards, the aforementioned two protrusions move a certain distance to the inside of the shell along the first guide groove 25, thereby driving the blade 32 to retract from the blade outlet to complete blood collection. FIG. 3 shows a view of the blade seat 30 retracting into the shell.

In the present disclosure, after the blood collection is completed, the bending portion of the elastic arm 12 abuts against the first cooperation column and does not pass over the first cooperation column 21 when the triggering portion rotates from the position shown in FIG. 3 to the position shown in FIG. 2, therefore the position of the blade seat 30 cannot be restored, and the reuse of the used blood collection device is avoid as a result.

It should be noted that, in the present disclosure, the blade outlet direction refers to the extension direction of the blade when the blade penetrates into the deepest position in the skin of the patient. Since the first guide groove 25 cooperates with the first protrusion 35 and the extension direction is generally the same as the blade outlet direction, after the second protrusion 36 is guided by the second guide portion 26 to enter the first guide groove 35, the blade 32 is in the blade outlet direction and will not move further in an arc, for example, move further leftward, so that the size of the blood collection knife edge can be effectively reduced when the penetration depth is the same.

In the present disclosure, the guide groove can be a concave groove formed in the wall of the shell, or a groove formed by a rib arranged to the wall of the shell.

In the present disclosure, although in the illustrated example, the spring provides power for the pivoting of the blade seat, the spring in the present disclosure also covers other elastic elements, which are all within the protection scope of the present disclosure. It should also be noted that in the illustrated embodiment, the spring is a tension spring, but the spring can also be a compression spring, and the compression spring pushes one end of the blade seat to push the blade seat to pivot. This is also within the protection scope of the present disclosure.

Although in the illustrated embodiment, the second guide portion 26 is in the form of a guide groove, as can be understood by those of ordinary skill in the art, the second guide portion 26 can also be a curved surface that limits the movement trajectory of the second protrusion 26. For example, the second guide portion 26 has an arc-shaped abutting surface centered on the first protrusion 35.

It should be pointed out that, in one embodiment of the present disclosure, only the elastic arm and the first cooperation column may be disposed, and the guide arm is not disposed.

Based on the above descriptions, the embodiments of the present disclosure propose the following technical solutions:

1. A blood collection device, comprising:
    a shell, wherein an accommodating cavity is formed in the shell, and the shell has a first opening and a second opening;
    a blade seat, pivotally arranged in the accommodating cavity, wherein a blade is arranged to the blade seat, and the blade is suitable for being exposed from the shell through the first opening when the blade seat pivots;
    an elastic component, arranged in the accommodating cavity, wherein one end of which is connected to the shell, and the other end of which is connected to the blade seat to provide an elastic force for pivoting the blade seat;
    a triggering portion, wherein the triggering portion comprises an operating end and an abutting end that are respectively arranged at two ends thereof, the triggering portion is suitable for pivoting around a pivot shaft arranged in the shell, the operating end extends from the second opening to the outside of the shell, the abutting end is located in the accommodating cavity, based on the operation of the operating end, the triggering portion is suitable for pivoting from a first position to a second position, at the first position, the abutting end is suitable for abutting against the blade seat 30 to prevent the blade seat from pivoting, and at the second position, the abutting end deviates from the blade seat to allow the blade seat to pivot based on the elastic force of the elastic component, wherein:
a first cooperation column is arranged in the shell and is located at the upper side of the triggering portion spaced from the triggering portion; and
an elastic arm is connected to the upper side of the triggering portion, the end part of the elastic arm is located in the accommodating cavity and comprises a blocking portion, the end part of the elastic arm is suitable for being located at one side of the first cooperation column when the triggering portion is at the first position, and is located at the other side of the first cooperation column when the triggering portion pivots from the first position to the second position, and the blocking portion provides resistance for the end part of the elastic arm while moving from one side of the first cooperation column to the other side.

2. The blood collection device according to 1, wherein:
the blocking portion comprises a bending portion that is bent upward, the bending portion is arranged in the accommodating cavity and is suitable for cooperating with the first cooperation column, the bending portion is suitable for abutting against the first cooperation column when the triggering portion is at the first position, the tail end of the bending portion is located at the one side of the first cooperation column and is suitable for disengaging from the first cooperation column based on the elasticity of the elastic arm during the process when the triggering portion pivots from the first position to the second position.

3. The blood collection device according to 2, wherein:
one side of the bending portion is suitable for abutting against the outer circumferential surface of the first cooperation column when the triggering portion is at the first position; and
during the process when the triggering portion rotates from the second position to the first position, the other side of the bending portion is suitable for abutting against the first cooperation column or abutting against the side wall of the shell at the other side of the first cooperation column to prevent the triggering portion from rotating from the second position to the first position.

4. The blood collection device according to 3, wherein:
the first cooperation column is a cylinder, the one side of the bending portion is a curved surface, and the other side of the bending portion is a curved surface.

5. The blood collection device according to 4, wherein:
the curved surface at the one side of the bending portion is suitable for engaging with around ¼ length of the circumference of the first cooperation column.

6. The blood collection device according to 2, wherein:
the first cooperation column is arranged in the vicinity of the side wall of the shell; and in the case that the triggering portion is at the first position, one side of the bending portion of the elastic arm is in contact with the first cooperation column, and during the process when the triggering portion moves from the second position to the first position, the other side of the bending portion of the elastic arm abuts against the first cooperation column and is suitable for moving toward the side wall of the shell.

7. The blood collection device according to any of 1-6, wherein:
a guide arm is arranged at the lower side of the triggering portion, and the guide arm forms an angle-shaped positioning groove with the main body of the triggering portion;
a second cooperation column is arranged in the shell; and
during the process when the triggering portion rotates from the first position to the second position, the guide arm is engaged with the second cooperation column, and at the second position, the second cooperation column is located in the angle-shaped positioning groove.

8. The blood collection device according to 7, wherein:
the one end of the elastic component is fixed to the second cooperation column.

9. The blood collection device according to 7, wherein:
a guide surface is arranged to the end part of the guide arm, the guide surface is suitable for guiding the guide arm to slide over the second cooperation column at the outer side of the second cooperation column, so that the second cooperation column enters the angle-shaped positioning groove.

10. The blood collection device according to 9, wherein:
the elastic arm and the guide arm are respectively arranged at the upper and lower sides of the triggering portion between the pivot shaft and the operating end.

11. The blood collection device according to any of 6-10, wherein:
the guide arm is a straight guide arm;
in the case that the triggering portion is at the first position, the guide arm is opposite to the second cooperation column; and
the distance between the second cooperation column and the pivot shaft is greater than or equal to the distance between an accommodating position of the angle-shaped positioning groove and the pivot shaft, and at the accommodating position, the second cooperation column is adapted to abut against the guide arm and the main body of the elastic arm at the same time.

12. The blood collection device according to 7, wherein:
the shell comprises a first shell portion and a second shell portion, and the pivot shaft, the first cooperation column and the second cooperation column are all arranged to the first shell portion;
the first shell portion is provided with a plurality of mounting columns, the second shell portion is provided with mounting holes that cooperate with the plurality of mounting columns, and the first shell portion and the second shell portion are engaged with each other based on the cooperation between the mounting columns and the mounting holes; and
the plurality of mounting columns comprise the first cooperation column and the second cooperation column.

13. The blood collection device according to any of 1-12, wherein:
a first protrusion and a second protrusion are arranged to the blade seat; and
the shell is provided with a first guide groove and a second guide portion, the first guide groove cooperates with the first protrusion, and the extension direction is substantially the same as the blade outlet direction, and the second guide portion cooperates with the second protrusion to guide the second protrusion to enter the first guide groove when the elastic component drives the blade seat to pivot.

14. The blood collection device according to 13, wherein:
the first guide groove has a first end close to the first opening and a second end far away from the first opening;
the second guide portion is connected to the first guide groove between the first end and the second end of the first guide groove; and
the elastic component is suitable for driving the blade seat to further move toward the second end of the first guide groove.

15. The blood collection device according to 14, wherein:
the second guide portion has an arc-shaped abutting surface centered on the first protrusion.

16. The blood collection device according to 15, wherein:
the second guide portion is a second guide groove, and the second guide groove has a first end far away from the first guide groove and a second end communicating with the first guide groove; and
when the abutting end abuts against the blade seat, the first protrusion pivotally abuts against the first end of the first guide groove, and the second protrusion pivotally abuts against the first end of the second guide groove.

17. The blood collection device according to 13, wherein:
the end of the blade seat close to the second protrusion has an abutting surface and an avoidance surface at both sides thereof, and the abutting end of the triggering portion is suitable for abutting against the abutting surface.

18. The blood collection device according to 17, wherein:
the end of the blade seat close to the second protrusion has a first step portion, a vertical surface of the first step portion parallel to the thickness direction of the blade seat forms a first abutting surface, and a horizontal plane of the first step portion vertical to the thickness direction of the blade seat forms a step surface; and
the abutting end has a blocking cooperation surface that is suitable for extending to cover the step surface and is vertical to the thickness direction of the blade seat, and the abutting end has a second abutting surface, and the second abutting surface is suitable for abutting against the first abutting surface to prevent the blade seat from pivoting.

19. The blood collection device according to 18, wherein:
the abutting end has a second step portion, a vertical surface of the second step portion parallel to the thickness direction of the abutting end forms the second abutting surface, and a plane of the second step portion vertical to the thickness direction of the abutting end forms the blocking cooperation surface.

20. A blood collection device, comprising:
a shell, wherein an accommodating cavity is formed in the shell, and the shell has a first opening and a second opening;
a blade seat, pivotally arranged in the accommodating cavity, wherein a blade is arranged to the blade seat, and the blade is suitable for being exposed from the shell through the first opening when the blade seat pivots;

an elastic component, arranged in the accommodating cavity, wherein one end of which is connected to the shell, and the other end of which is connected to the blade seat to provide an elastic force for pivoting the blade seat;

a triggering portion, wherein the triggering portion comprises an operating end and an abutting end that are respectively arranged at two ends thereof, the triggering portion is suitable for pivoting around a pivot shaft arranged in the shell, the operating end extends from the second opening to the outside of the shell, the abutting end is located in the accommodating cavity, based on the operation of the operating end, the triggering portion is suitable for pivoting from a first position to a second position, at the first position, the abutting end is suitable for abutting against the blade seat to prevent the blade seat from pivoting, and at the second position, the abutting end deviates from the blade seat to allow the blade seat to pivot based on the elastic force of the elastic component, wherein:

a first cooperation column is arranged in the shell and is located at the upper side of the triggering portion spaced from the triggering portion;

a second cooperation column is arranged in the shell and is located at the lower side of the triggering portion spaced from the triggering portion;

an elastic arm is connected to the upper side of the triggering portion, the end part of the elastic arm is provided with a bending portion, the bending portion is arranged in the accommodating cavity and is suitable for cooperating with the first cooperation column, in the case that the triggering portion is at the first position, an upper side face of the bending portion abuts against an outer circumferential surface on the lower side of the first cooperation column;

the tail end of the bending portion is bent upward to provide resistance for the elastic arm to disengage from the first cooperation column when the triggering portion is at the first position; and a guide arm is connected to the lower side of the triggering portion, and during the process when the triggering portion rotates from the first position to the second position, the guide arm is suitable for sliding over the second cooperation column at the outer side of the second cooperation column when abutting against the outer circumferential surface of the second cooperation column.

21. The blood collection device according to 20, wherein:

a guide surface is arranged to the end part of the guide arm, and the guide surface is suitable for guiding the guide arm to slide over the second cooperation column at the outer side of the second cooperation column during the process when the triggering portion rotates from the first position to the second portion.

22. The blood collection device according to 21, wherein:

one side of the bending portion is suitable for abutting against the outer circumferential surface of the first cooperation column when the triggering portion is at the first position; and during the process when the triggering portion rotates from the second position to the first position, the other side of the bending portion is suitable for abutting against the first cooperation column, or the tail end of the bending portion is suitable for abutting between the first cooperation column and the side wall of the shell to prevent the triggering portion from rotating from the second position to the first position.

The blood collection device based on the technical solutions of the present disclosure has a simple structure and few components, and the blood collection operation of the entire blood collection device can be controlled through the operation of one triggering portion.

Although the embodiments of the present disclosure have been shown and described, those of ordinary skill in the art can understand that changes can be made to these embodiments without departing from the principle and spirit of the present disclosure, and the scope of the present disclosure is defined by the appended claims and their equivalents.

The invention claimed is:

1. A blood collection device, comprising:

a shell (20), wherein an accommodating cavity is formed in the shell, and the shell has a first opening (20A) and a second opening (20B);

a blade seat (30), pivotally arranged in the accommodating cavity, wherein a blade is arranged to the blade seat, and the blade is suitable for being exposed from the shell through the first opening (20A) when the blade seat pivots;

an elastic component (40), arranged in the accommodating cavity, wherein one end of which is connected to the shell, and another end of which is connected to the blade seat to provide an elastic force for pivoting the blade seat;

a triggering portion (10), wherein the triggering portion comprises an operating end (11) and an abutting end (16) that are respectively arranged at two ends thereof, the triggering portion is suitable for pivoting around a pivot shaft (23) arranged in the shell, the operating end extends from the second opening (20B) to the outside of the shell, the abutting end is located in the accommodating cavity, based on an operation of the operating end, the triggering portion is suitable for pivoting from a first position to a second position, at the first position, the abutting end is suitable for abutting against the blade seat (30) to prevent the blade seat from pivoting, and at the second position, the abutting end deviates from the blade seat to allow the blade seat to pivot based on the elastic force of the elastic component, wherein:

a first cooperation column (21) is arranged in the shell and is located at an upper side of the triggering portion spaced from the triggering portion; and an elastic arm (12) is connected to the upper side of the triggering portion, an end part of the elastic arm is located in the accommodating cavity and comprises a blocking portion, the end part of the elastic arm is suitable for being located at one side of the first cooperation column when the triggering portion is at the first position, and is located at an other side of the first cooperation column when the triggering portion pivots from the first position to the second position, and the blocking portion provides resistance for the end part of the elastic arm while moving from one side of the first cooperation column to the other side.

2. The blood collection device according to claim 1, wherein:

the blocking portion comprises a bending portion that is bent upward, the bending portion is arranged in the accommodating cavity and is suitable for cooperating with the first cooperation column, the bending portion is suitable for abutting against the first cooperation column when the triggering portion is at the first position, a tail end of the bending portion is located at the one side of the first cooperation column and is suitable for disengaging from the first cooperation column based on an elasticity of the elastic arm during a process when the triggering portion pivots from the first position to the second position.

3. The blood collection device according to claim 2, wherein:
one side of the bending portion is suitable for abutting against an outer circumferential surface of the first cooperation column when the triggering portion is at the first position; and
during the process when the triggering portion rotates from the second position to the first position, an other side of the bending portion is suitable for abutting against the first cooperation column or abutting against a side wall of the shell at the other side of the first cooperation column to prevent the triggering portion from rotating from the second position to the first position.

4. The blood collection device according to claim 3, wherein:
the first cooperation column is a cylinder, the one side of the bending portion comprises a curved surface, and the other side of the bending portion comprises a curved surface.

5. The blood collection device according to claim 4, wherein:
the curved surface at the one side of the bending portion is suitable for engaging with around ¼ length of the circumference of the first cooperation column.

6. The blood collection device according to claim 2, wherein:
the first cooperation column is arranged in the vicinity of the side wall of the shell; and
in the case that the triggering portion is at the first position, one side of the bending portion of the elastic arm is in contact with the first cooperation column, and during the process when the triggering portion moves from the second position to the first position, the other side of the bending portion of the elastic arm abuts against the first cooperation column and is suitable for moving toward the side wall of the shell.

7. The blood collection device according to claim 6, wherein:
a guide arm is a straight guide arm;
in the case that the triggering portion is at the first position, the guide arm is opposite to a second cooperation column; and
a distance between the second cooperation column and the pivot shaft is greater than or equal to the distance between an accommodating position of an angle-shaped positioning groove and the pivot shaft, and at the accommodating position, the second cooperation column is adapted to abut against the guide arm and a main body of the elastic arm at the same time.

8. The blood collection device according to claim 1, wherein:
a guide arm (13) is arranged at a lower side of the triggering portion, and the guide arm forms an angle-shaped positioning groove (15) with a main body (14) of the triggering portion;
a second cooperation column (22) is arranged in the shell; and
during the process when the triggering portion rotates from the first position to the second position, the guide arm is engaged with the second cooperation column, and at the second position, the second cooperation column is located in the angle-shaped positioning groove.

9. The blood collection device according to claim 8, wherein:
the one end of the elastic component is fixed to the second cooperation column.

10. The blood collection device according to claim 8, wherein:
a guide surface (131) is arranged to the end part of the guide arm, the guide surface is suitable for guiding the guide arm to slide over the second cooperation column at the outer side of the second cooperation column, so that the second cooperation column enters the angle-shaped positioning groove.

11. The blood collection device according to claim 10, wherein:
the elastic arm and the guide arm are respectively arranged at the upper and lower sides of the triggering portion between the pivot shaft and the operating end.

12. The blood collection device according to claim 8, wherein:
the shell comprises a first shell portion and a second shell portion, and the pivot shaft, the first cooperation column and the second cooperation column are arranged to the first shell portion;
the first shell portion is provided with a plurality of mounting columns, the second shell portion is provided with mounting holes that cooperate with the plurality of mounting columns, and the first shell portion and the second shell portion are engaged with each other based on the cooperation between the mounting columns and the mounting holes; and
the plurality of mounting columns comprise the first cooperation column and the second cooperation column.

13. The blood collection device according to claim 1, wherein:
a first protrusion and a second protrusion are arranged to the blade seat; and
the shell is provided with a first guide groove and a second guide portion, the first guide groove cooperates with the first protrusion and an extension direction thereof is substantially the same as a blade outlet direction, and the second guide portion cooperates with the second protrusion to guide the second protrusion to enter the first guide groove when the elastic component drives the blade seat to pivot.

14. The blood collection device according to claim 13, wherein:
the first guide groove has a first end close to the first opening and a second end far away from the first opening;
the second guide portion is connected to the first guide groove between the first end and the second end of the first guide groove; and
the elastic component is suitable for driving the blade seat to further move toward the second end of the first guide groove.

15. The blood collection device according to claim 14, wherein:
the second guide portion has an arc-shaped abutting surface centered on the first protrusion.

16. The blood collection device according to claim 15, wherein:
the second guide portion is a second guide groove, and the second guide groove has a first end far away from the first guide groove and a second end communicating with the first guide groove; and when the abutting end abuts against the blade seat, the first protrusion pivotally abuts against the first end of the first guide groove, and the second protrusion pivotally abuts against the first end of the second guide groove.

17. The blood collection device according to claim 13, wherein:

an end of the blade seat close to the second protrusion has an abutting surface and an avoidance surface at both sides thereof, and the abutting end of the triggering portion is suitable for abutting against the abutting surface.

18. The blood collection device according to claim 17, wherein:

the end of the blade seat close to the second protrusion has a first step portion, a vertical surface of the first step portion parallel to a thickness direction of the blade seat forms a first abutting surface, and a horizontal plane of the first step portion vertical to the thickness direction of the blade seat forms a step surface; and the abutting end has a blocking cooperation surface that is suitable for extending to cover the step surface and is vertical to the thickness direction of the blade seat, and the abutting end has a second abutting surface, and the second abutting surface is suitable for abutting against the first abutting surface to prevent the blade seat from pivoting.

19. The blood collection device according to claim 18, wherein:

the abutting end has a second step portion, a vertical surface of the second step portion parallel to the thickness direction of the abutting end forms the second abutting surface, and a plane of the second step portion vertical to the thickness direction of the abutting end forms the blocking cooperation surface.

20. A blood collection device, comprising:

a shell (20), wherein an accommodating cavity is formed in the shell, and the shell has a first opening (20A) and a second opening (20B);

a blade seat (30), pivotally arranged in the accommodating cavity, wherein a blade is arranged to the blade seat, and the blade is suitable for being exposed from the shell through the first opening (20A) when the blade seat pivots;

an elastic component (40), arranged in the accommodating cavity, wherein one end of which is connected to the shell, and an other end of which is connected to the blade seat to provide an elastic force for pivoting the blade seat;

a triggering portion (10), wherein the triggering portion comprises an operating end (11) and an abutting end (16) that are respectively arranged at two ends thereof, the triggering portion is suitable for pivoting around a pivot shaft (23) arranged in the shell, the operating end extends from the second opening (20B) to the outside of the shell, the abutting end is located in the accommodating cavity, and based on an operation of the operating end, the triggering portion is suitable for pivoting from a first position to a second position, at the first position, the abutting end is suitable for abutting against the blade seat (30) to prevent the blade seat from pivoting, and at the second position, the abutting end deviates from the blade seat to allow the blade seat to pivot based on the elastic force of the elastic component, wherein:

a first cooperation column (21) is arranged in the shell and is located at an upper side of the triggering portion spaced from the triggering portion;

a second cooperation column (22) is arranged in the shell and is located at a lower side of the triggering portion spaced from the triggering portion;

an elastic arm (12) is connected to the upper side of the triggering portion, an end part of the elastic arm is provided with a bending portion, the bending portion is arranged in the accommodating cavity and is suitable for cooperating with the first cooperation column, in the case that the triggering portion is at the first position, an upper side face of the bending portion abuts against an outer circumferential surface on a lower side of the first cooperation column;

a tail end of the bending portion is bent upward to provide resistance for the elastic arm to disengage from the first cooperation column when the triggering portion is at the first position; and a guide arm is connected to the lower side of the triggering portion, and during a process when the triggering portion rotates from the first position to the second position, the guide arm is suitable for sliding over the second cooperation column at an outer side of the second cooperation column when abutting against the outer circumferential surface of the second cooperation column.

* * * * *